(12) United States Patent
Houfburg et al.

(10) Patent No.: US 6,171,339 B1
(45) Date of Patent: Jan. 9, 2001

(54) MULTI-LUMEN SPINAL IMPLANT GUIDE AND METHOD

(75) Inventors: Rodney L. Houfburg, Prior Lake; Richard A. Erickson, Edina, both of MN (US)

(73) Assignee: Sulzer Spine-Tech Inc., Minneapolis, MN (US)

( * ) Notice: Under 35 U.S.C. 154(b), the term of this patent shall be extended for 0 days.

(21) Appl. No.: 09/081,240

(22) Filed: May 19, 1998

(51) Int. Cl.[7] .................................. A61F 5/04; A61F 2/44
(52) U.S. Cl. .................................................. 623/17; 606/61
(58) Field of Search ........................... 606/61, 60, 72–79; 623/16, 1.7

(56) References Cited

U.S. PATENT DOCUMENTS

| | | |
|---|---|---|
| D. 397,436 | 8/1998 | Michelson . |
| 5,026,373 | 6/1991 | Ray et al. . |
| 5,055,104 | 10/1991 | Ray . |
| 5,484,437 | 1/1996 | Michelson . |
| 5,489,307 | 2/1996 | Kushlich et al. . |
| 5,505,732 | 4/1996 | Michelson . |
| 5,593,409 | 1/1997 | Michelson . |
| 5,700,291 | 12/1997 | Kuslich et al. . |
| 5,720,748 | 2/1998 | Kushlich et al. . |
| 5,741,253 | 4/1998 | Michelson . |
| 5,797,909 | 8/1998 | Michelson . |

FOREIGN PATENT DOCUMENTS

| | | |
|---|---|---|
| 0 796 593 A2 | 9/1997 | (EP) . |
| WO 91/06261 | 5/1991 | (WO) . |
| WO 94/28824 | 12/1994 | (WO) . |
| WO 97/23174 | 7/1997 | (WO) . |
| WO 98/17208 | 4/1998 | (WO) . |

OTHER PUBLICATIONS

Sofamor Danek Brochure: "Surgical Technique Using Bone Dowel Instrumentation."

Sulzer Spine—Tech Brochure: Anterior, 4021 Tooth Tube Surgical Technique, BAK™ Interbody Fusion System.

*Primary Examiner*—Todd E. Manahan
(74) *Attorney, Agent, or Firm*—Merchant & Gould P.C

(57) ABSTRACT

The present invention provides instruments and methods for insertion of multiple spinal implants into the intervertebral space between opposing vertebral bodies. Instrumentation according to the invention includes a multi-lumen guide, complimentary obturators, drill depth guides and other associated instruments. The methods of the invention provide for greater ease and accuracy in aligning multiple spinal implants in an intervertebral disk space.

23 Claims, 6 Drawing Sheets

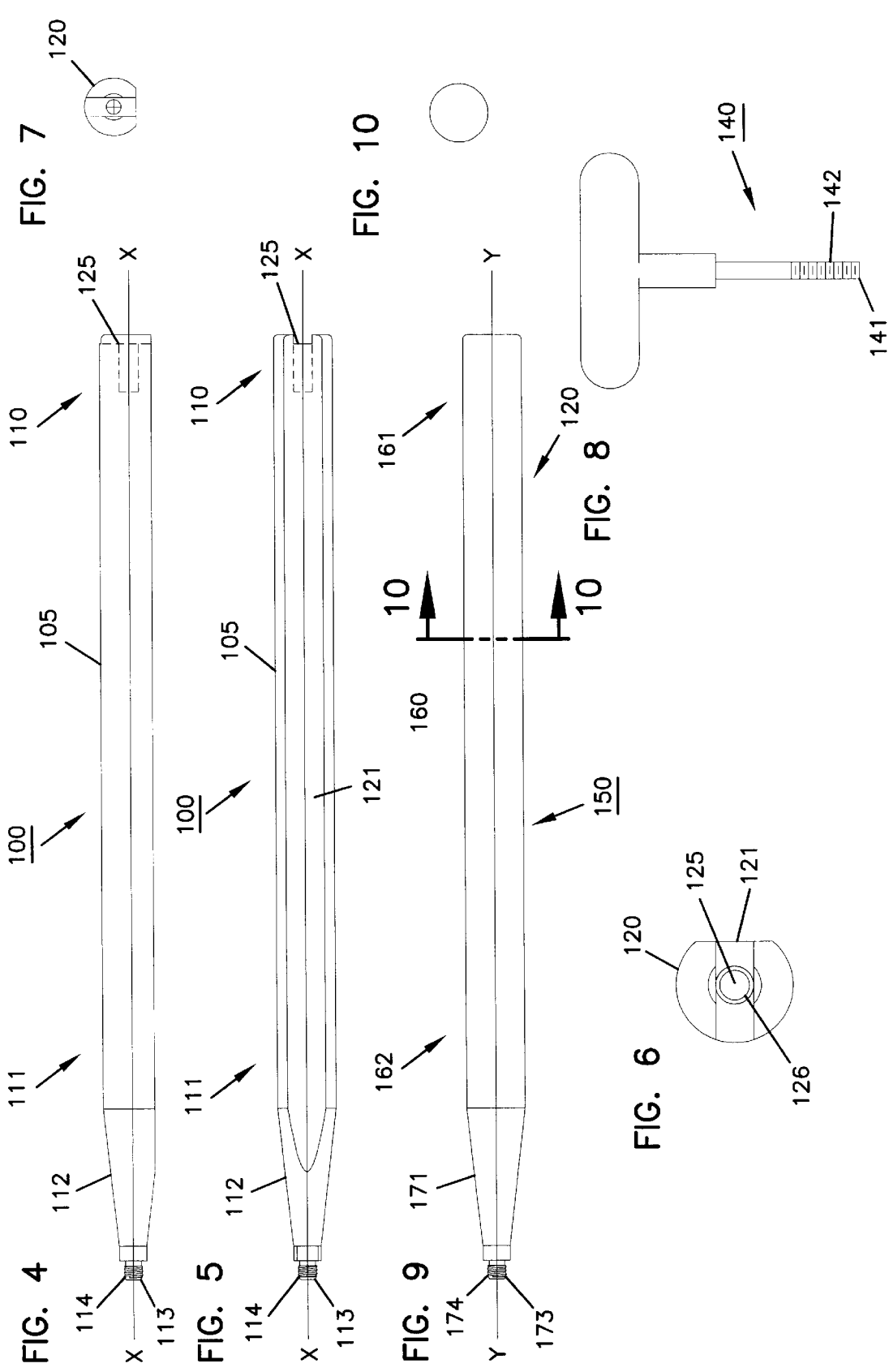

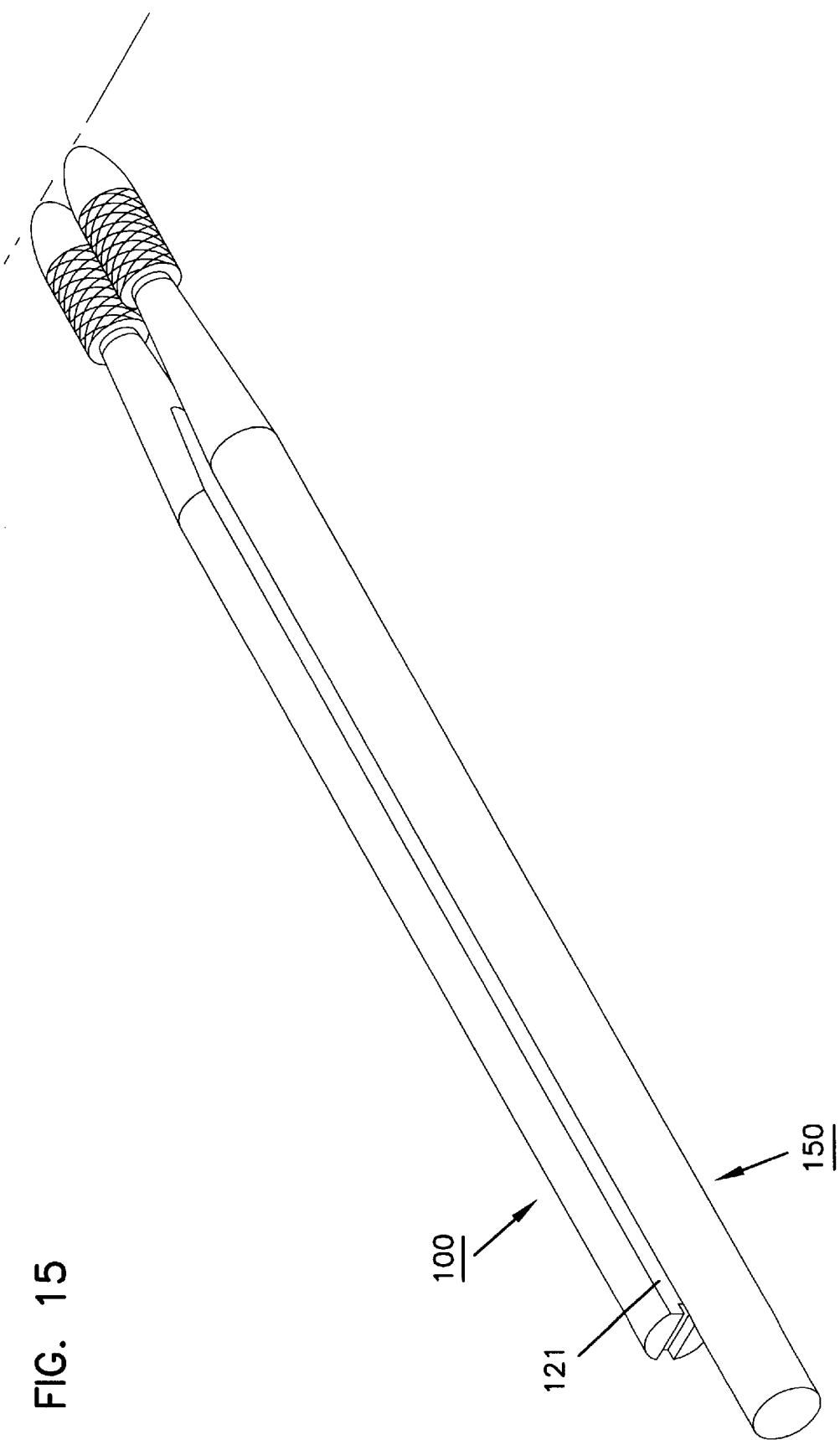

MULTI-LUMEN SPINAL IMPLANT GUIDE AND METHOD

FIELD OF THE INVENTION

This invention pertains to intervertebral fusion. Specifically, the invention is directed to instrumentation and methods for insertion of spinal implants between opposing vertebral bodies.

BACKGROUND OF THE INVENTION

Chronic back problems can cause pain and disability for a large segment of the population. Frequently, the cause of back pain is traceable to diseased disk material between opposing vertebrae. When the disk material is diseased, the opposing vertebrae may be inadequately supported, resulting in persistent pain.

Surgical techniques have been developed to remove the diseased disk material and fuse the joint between opposing vertebral bodies. Arthrodesis of the intervertebral joint can reduce the pain associated with movement of an intervertebral joint having diseased disk material. Generally, fusion techniques involve removal of the diseased disk, drilling a bore for receiving the implant and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; and 4,961,740.

Procedures for fusing an intervertebral joint space typically include placement of at least two cylindrical implants in parallel arrangement between the opposing vertebrae. Recently, non-circular implants have been introduced that provide for placing parallel implants in close proximity to one another. Examples of such implants are disclosed in, for example, U.S. Pat. Nos. 5,658,337; 5,593,409; and 5,489,307, the entire disclosures of which are incorporated herein by reference. These non-circular implants may be referred to as reduced lateral profile (RLP) implants and typically have a side wall geometry that permits placement of two RLP implants or one RLP and one cylindrical implant in closer proximity to one another. Thus, greater surface area support of the intervertebral space and/or increased distraction of the disk space can be provided for a given medial/lateral dimension of the vertebral body.

Some presently available systems for implanting fusion devices permit for preparing an implant site through a hollow tube. Procedures for preparing an implant site through a single hollow tube are shown in, for example, U.S. Pat. Nos. 5,505,732; 5,484,437; and 5,489,307. The disclosure of each of these patents are incorporated herein by reference. In some procedures, the implants are also inserted into the prepared site through the hollow tube. Preparing the implant site by passing instruments through a hollow tube advantageously provides for an isolated surgical field with reduced chance of injury to soft tissues surrounding the surgical site.

However, generally, several steps are required for appropriate placement of the implants using present hollow tube systems. These steps include inserting a spacer into the disk space to distract one side of the intervertebral space, then inserting a second spacer for distracting the second side of the vertebral space, followed by placement of the hollow tube over a guiding mechanism to orient the longitudinal angulation of the implant site. Once the hollow tube is secured in proper alignment, reamers, bores, taps, or other instruments are passed through the hollow tube to prepare the implant site. Either before or after the implant is inserted into the first site, the hollow tube is removed and the procedure is repeated on the opposite side.

Present procedures for placement of an implant through a hollow tube help to reduce the chance of iatrogenic tissue trauma caused by the implant procedure. However, while known procedures provide for reduced chance of injury, the surgeon's accuracy in the relative placement of the hollow tube between the first and second sides is still a matter of guess work and repeated verification using fluoroscopy or radiographic monitoring is needed. Also, the need for separate placement of the hollow guide tube using present methods (i.e., one placement for each implant) increases the possibility for relative misalignment of the implants to occur during insertion.

Thus, there is a continuing need for the precision, safety and ease of placement of spinal fusion implants. There is also a need for implant insertion systems that accommodate implants having non-circular cross-sectional geometries. The present invention is directed to addressing these needs.

SUMMARY OF THE INVENTION

The present invention increases the ease and enhances the precision of placement of spinal fusion implants between opposing vertebral bodies. Spinal implant procedures using the instrumentation and methods of the invention also reduce the number of steps necessary for implantation. The invention is particularly advantageous for inserting implants in close proximity.

Throughout the specification, guidance may be provided through lists of examples. In each instance, the recited list serves only as a representative group. It is not meant, however, that the list is exclusive.

In one embodiment, the invention provides a multi-lumen guide for preparing a spinal implant surgical field. In a preferred embodiment, the multi-lumen guide provides a surgical field for insertion of spinal implants in close proximity. According to this embodiment, the multi-lumen guide includes a first elongate lumen having a first cross-sectional geometry and a second elongate lumen having a second cross-sectional geometry. The elongate lumens are adjacent and parallel to one another with overlapping cross-sectional geometries. In one embodiment, the cross-sectional geometry of at least one of the lumens is circular.

At the distal end, a multi-lumen guide can include an anchoring arrangement for securing the guide to the vertebral bodies. The anchoring arrangement can include teeth which can be embedded into the vertebral body. In addition, the distal end of the guide can include one or more laterally positioned paddles which help reduce the chance of tissues outside the surgical field entering into the surgical field. In a preferred embodiment, one or more of the walls of the multi-lumen guide can also include an opening, such as a longitudinal slot, which, in addition to other advantages, facilitates cleaning of the guide.

The multi-lumen guide can be included in a kit also including one obturator for each lumen. For a multi-lumen guide having a circular cross-sectional geometry, at least one of the obturators is also circular. If the lumens of the multi-lumen guide have an overlapping circular geometry, at least one obturator has an elongate flat surface parallel to the longitudinal axis of the obturator. Preferably the obturators also have an attachment system for attaching a distraction spacer to the obturator.

The invention also provides a drill depth guide. In one embodiment, the drill depth guide is a spacer cap that can be placed at the proximal end of the multi-lumen guide to control the depth of a bore made into the vertebral bodies during a procedure according to the invention.

The invention also provides a method for implanting a spinal implant into a disk space between opposing vertebral bodies. The method is particularly advantageous for placement of two spinal implants in close proximity. According to the method, a first distraction spacer is placed into a first side of a disk space between opposing vertebral bodies and a second distraction spacer is placed into the second side of the disk space. A first lumen is then placed across the first side of the disk space over the first distraction spacer and a second guide lumen is placed across the second side of the disk space over the second distraction spacer. Subsequently, one of the distraction spacers is removed for preparing a first bore for receiving a spinal implant. After preparing the first bore, a second bore is prepared. As described herein, in a preferred embodiment, the first and second distraction spacers are placed into the disk space simultaneously. In addition, a multi-lumen guide of the invention also provides for simultaneously positioning of the first and second guide lumens across the disk space.

BRIEF DESCRIPTION OF THE DRAWINGS

FIG. 4 is a side view of an embodiment of a reduced lateral profile obturator of the invention;

FIG. 5 is a side view of the embodiment of the obturator of FIG. 4 rotated 90°;

FIG. 6 is an end-on view of the proximal end of the obturator of FIG. 4;

FIG. 7 is an end-on view of the distal end of the obturator of FIG. 6;

FIG. 8 is an embodiment of a handle for attaching to an obturator such as that illustrated in FIGS. 4–7;

FIG. 9 is an embodiment of a cylindrical obturator according to the invention;

FIG. 10 is a cross-section view taken through 10—10 of the obturator of FIG. 9;

FIG. 13b is a short side view of the embodiment of a drill depth guide of FIG. 13a.

FIG. 15 illustrates alignment of the distal ends of two distraction spacers attached to obturators;

DETAILED DESCRIPTION OF THE INVENTION

The instruments and methods of the present invention facilitate the ease and accuracy of placement of multiple spinal implants into a vertebral space between opposing vertebrae. The complementary interaction of the herein disclosed component instruments can also reduce the number of intraoperative images needed to establish the relative alignment of the implants during an implant procedure.

The ability to enhance the accuracy of alignment between two implants inserted into the intervertebral disk space according to the procedures of the invention is facilitated by early establishment and continued maintenance of parallel operating fields at multiple implant sites. Once the surgeon has determined the angular orientation of the implant (e.g., relative to the sagittal and/or transverse plane of the vertebral column), the instrumentation disclosed ensures that the relative positioning of the implants is maintained throughout preparation of the bores that will receive the implants.

Some instruments useful with the new instruments described herein are known and disclosed in, for example, U.S. Pat. No. 5,489,307 and co-pending patent application Ser. Nos. 09/045,213 and 09/036,165, the entire disclosures of which are incorporated herein by reference. These disclosures include various distraction plugs, guide pins, reamers, taps, etc., some which are described in more detail below.

It will be appreciated that the present procedures are applicable for use with a wide variety of implants including threaded implants and non-threaded implants. The term "implant" as used herein includes bone implants (e.g., autograft, allograft, artificial bone) and non-bone implants made from titanium or other implantable material. In preferred embodiments, the instruments and methods disclosed are advantageously used for insertion of implants having a reduced lateral profile as disclosed in U.S. Pat. Nos. 5,609,636, 5,658,337 and co-pending patent application Ser. Nos. 09/045,213 and 09/036,165, the entire disclosures of which have previously been incorporated herein. In one embodiment, the instruments and methods of the invention can advantageously be used for insertion of a reduced lateral profile implant adjacent to a cylindrical implant such as disclosed in U.S. Pat. Nos. 5,609,636 and 5,658,337.

Detailed Description of the Illustrated Embodiment

Referring to the several drawing figures in which identical elements are numbered identically throughout, a description of embodiments of the invention will now be provided.

1. Instruments

A. Multi-Lumen Guide

Figure 1:
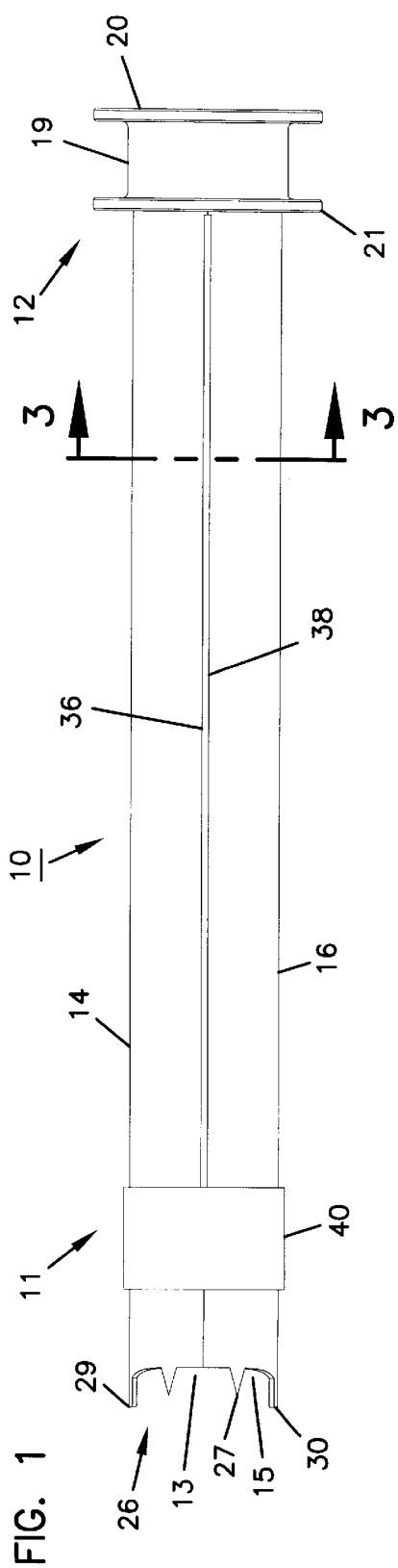
FIG. 1 is a top plan view of a multi-lumen guide according to the invention.
Figure 2:
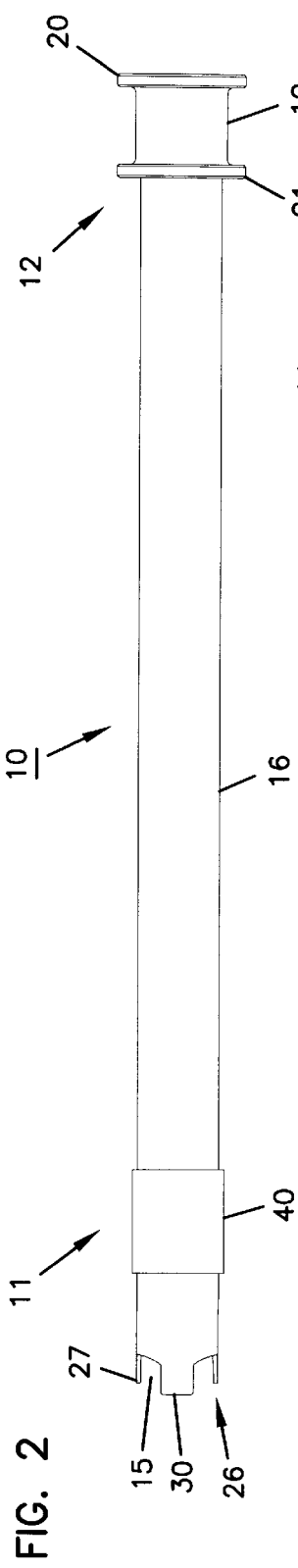
FIG. 2 is a side view of the multi-lumen guide of FIG. 1.
Figure 3:
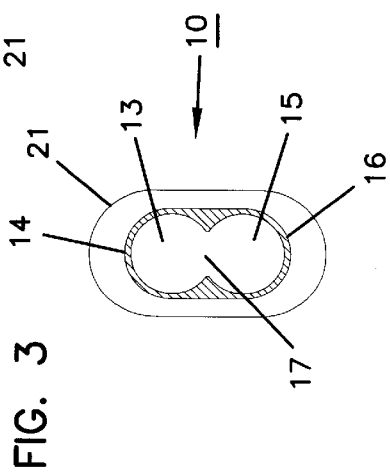
FIG. 3 is a cross-section view taken through 3—3 of the multi-lumen guide of FIG. 1.
Figure 14:
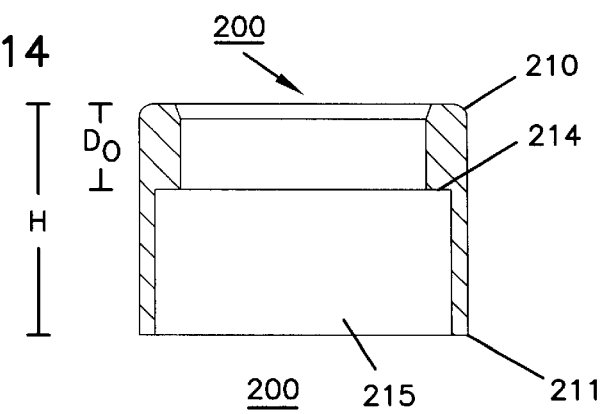
FIG. 14 is a longitudinal cross-section view taken through line 14—14 of the drill depth guide of FIG. 13.

FIGS. 1–3 illustrate one embodiment of a multi-lumen guide 10. Multi-lumen guide 10 includes a distal end 11 and a proximal end 12. The top plan view of FIG. 1 illustrates that multi-lumen guide 10 includes a first elongate lumen 13 surrounded by an elongate wall 14 and a second elongate lumen 15 surrounded by elongate wall 16. Referring to FIG. 3, taken at line 3—3 of FIG. 1, it will be appreciated that in the illustrated embodiment the cross-sectional geometry of each of elongate lumens 13 and 15 is circular. The elongate walls 14 and 16 defining lumens 13 and 15 are incomplete at common region 17 where the circular geometry of lumen 13 and lumen 15 overlap one another. The overlapping geometry of the cross-sectional surface area of lumens 13 and 15 provides for reducing the spacing between the longitudinal axes of parallel spinal fusion implants when using multi-lumen guide 10.

The cross-sectional diameter of each of lumens 13 and 15 can be the same. Different multi-lumen guides 10 can be provided for different size spinal implants. However, it is foreseen that an individual multi-lumen guide having two lumens with different diameters could also be advantageous for some procedures. Generally the lumen diameters are selected for the passage of the instrumentation necessary to insert a particular size implant. Some presently available implants have a diameter of 11, 13, 15, 17 or 19 mm.

The illustrated multi-lumen guide 10 includes a proximal collar 19 at proximal end 12 and a distal collar 40 at distal end 11. The collars maintain walls 14 and 16 in a parallel relationship. In addition, when the walls of the elongate lumens are incomplete, for example at common region 17, the collars can maintain the size of the outer and inner diameters of the lumens and provide for consistent spacing between the longitudinal axes of the implants. The proximal collar 19 has a proximal flange 20 spaced apart from a distal flange 21. One advantage of a flanged collar is that the perimeter dimension of the flange can be constant among multi-lumen guides having different lumen diameters. Thus, instruments that may be used with the multi-lumen guide, such as the below-described drill depth guide, can be sized to fit with the flange of a multi-lumen guide regardless of lumen size.

At the distal end 11, multi-lumen guide 10 includes an anchoring arrangement 26 for attaching the multi-lumen guide 10 to opposing vertebral bodies. In the illustrated embodiment, the anchoring arrangement includes teeth 27. In addition, near the anchoring arrangement, the multi-lumen guide 10 also includes lateral paddles 29 and 30 on diametrically opposed aspects of adjacent walls 14 and 16, respectively. In use, these paddles can be inserted into the intervertebral disk space and function to keep blood vessels or other tissues outside the surgical field within the multi-lumen guide 10.

The walls surrounding lumens 13 and 15 do not need to be complete. In the embodiment of FIG. 1, walls 14 and 16 can also each include one or more openings such as elongate slots 36 and 38 along some or all of the length of wall 14 and 16. The openings of slots 36 and 38 provide for easier cleaning of multi-lumen guide 10.

B. Obturator

Referring now to FIGS. 4–7, one embodiment of an obturator 100 of the invention will be described. In this embodiment, the obturator includes a shaft 105 having a proximal end 110 and a distal end 111. In the illustrated embodiment, the proximal end 111 includes a taper 112 and a male end 113. The male end 113 can include threads 114 for attachment of the distal end 111 of obturator 100 to the proximal end of a distraction spacer such as that illustrated in FIG. 28 of U.S. Pat. No. 5,489,307. In some embodiments, a flange may be present immediately proximal to the male end 113. This flange can act as a positive stop to limit the depth of insertion of a distraction plug into the intervertebral space.

FIGS. 6 and 7 are proximal and distal end-on views, respectively, of obturator 100. As illustrated, the cross section of shaft 105 of obturator 100 has a substantially circular configuration 120 with a flat surface 121. The flat surface 121 of shaft 105 is parallel to the longitudinal access X—X of obturator 100. Flat surface 121 provides a reduced lateral profile (RLP) to obturator 100 for passage into a lumen of multi-lumen guide 10 when a second obturator having a full lateral profile (described below) is passed into a second lumen of multi-lumen 10. The RLP obturator 100 facilitates parallel and proximate implant alignment when used with a multi-lumen guide having overlapping lumenal geometry.

The proximal end 110 of obturator 100 includes a bore 125 which can be threaded 126. A threaded 126 bore 125 of obturator 100 provides for attachment of a handle, such as T-handle 140 illustrated in FIG. 8. As illustrated, T-handle 140 includes a male end 141 having threads 142 complementary to threads 126 of bore 125. Attaching a handle, such as T-handle 140, to obturator 100 provides a grip for removing obturator 100 from multi-lumen guide 10.

Referring to FIGS. 9 and 10, a full lateral profile (i.e., cylindrical) obturator 150 having a longitudinal axis Y—Y is illustrated. Obturator 150 includes a shaft 160 having a proximal end 161 and a distal end 162. FIG. 10 is a cross-section view taken at 10—10 of FIG. 9 illustrating the lack of a flat surface in cylindrical obturator 150. For reasons discussed below, obturator 150 may be longer than RLP obturator 100. (See FIG. 15). The extended length of obturator 150 provides a handle region 170 for grasping obturator 150 at the proximal end 161. The distal end 162 of shaft 160 of obturator 150 includes a taper 171 and a male end 173 having threads 174 for attachment to a distraction spacer, as described above, for obturator 100. Also, as described above for an RLP obturator, a flange may be present immediately proximal to the male end to act as a positive stop to insertion depth.

C. Drill Depth Guide

Figure 13:
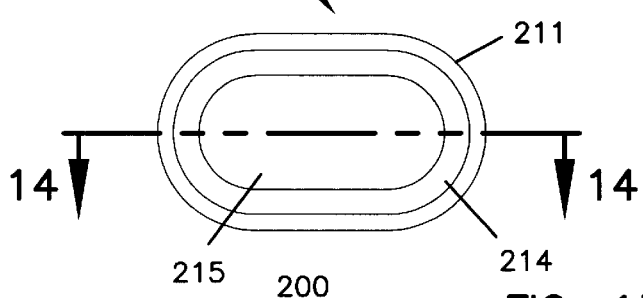
FIG. 13 is an end-on view through the distal end of the drill depth guide of FIG. 11.
Figure 12:
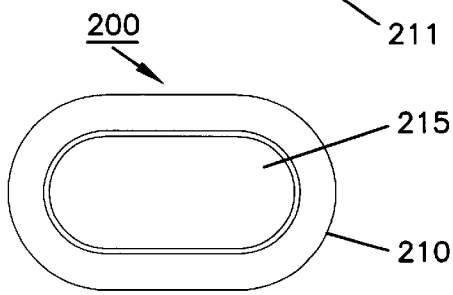
FIG. 12 is an end-on view through the proximal end of the drill depth guide of FIG. 11.

FIGS. 11–14 illustrate a drill depth guide referred to as a spacer cap 200. Spacer cap 200 can be removably mounted to the proximal end 12 of multi-lumen guide 10 for selectively adjusting the depth of a bore formed into opposing vertebral bodies by a boring tool passed through multi-lumen guide 10. The illustrated spacer cap 200 is oval shaped for complementary fit at the proximal end 12 of multi-lumen guide 10. FIG. 12 is an end-on view of the proximal end 210 of spacer cap 200 and FIG. 13 is an end-on view the distal end 211 of spacer cap 200. As illustrated in cross-section view 14 taken through line 14—14 of FIG. 13, spacer cap 200 includes a shoulder 214 projecting axially into the lumen 215 of the spacer cap 200. For a given spacer cap height H, the distance $D_0$ between shoulder 214 and the proximal end 211 of spacer cap 200 is equal to the length of spacer cap 200 that extends distally beyond the proximal end 12 of multi-lumen guide 10. In the illustrated embodiment, when in use, shoulder 214 is seated on the proximal flange 20 of proximal collar 19.

Providing multiple spacer caps, each having a different distance $D_0$, will permit the surgeon to select a spacer cap having the appropriate distance $D_0$ for drilling a selected bore depth into opposing vertebrae through multi-lumen guide 10. Increasing distance $D_0$ directly decreases the depth of a bore that can be made in the vertebral bodies by a particular boring tool passed through multi-lumen guide 10.

Figure 13A:
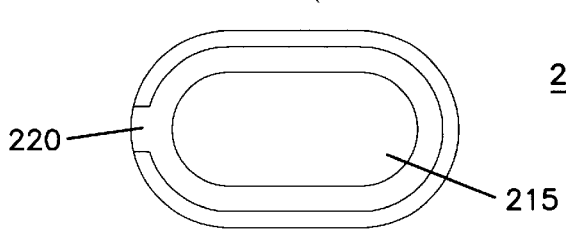
FIG. 13a is an end-on view of the distal end of a second embodiment of a drill depth guide.
Figure 13B:
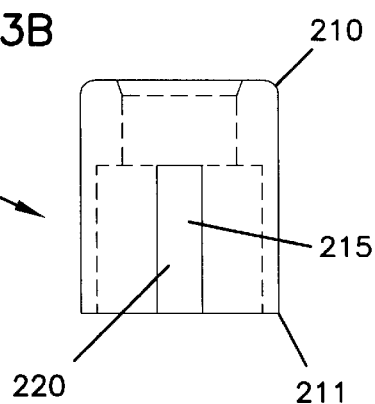
Figure 11:
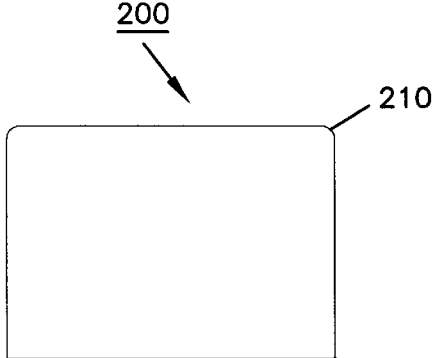
FIG. 11 is a long side view of an embodiment of a drill depth guide of the invention.

Referring to FIGS. 13a and 13b, in some embodiments, a spacer cap 200 can include a slot 220 extending from the distal end 211 of spacer cap 200. The slot 220 may or may not exit the proximal end 210 of the spacer cap 200. Slot 220 provides for expansion of the size of spacer cap lumen 215 to permit the spacer cap 200 to be slid laterally onto the proximal end 12 of the multi-lumen guide 10, rather than over the proximal end.

A procedure for inserting a spinal implant using a multi-lumen guide according to the invention is described below. Some suitable reamers, taps, guide pins or other instruments for performing an implantation procedure in the surgical field of a herein described multi-lumen device are known and described in, for example, U.S. Pat. No. 5,489,307 which has previously been incorporated herein by reference.

II. Methods

A surgical procedure for inserting an intervertebral fusion implant with a multi-lumen guide according to the invention is most advantageously performed through an anterior approach. In an anterior approach, the surgeon seeks access to the vertebral column through the abdomen of a patient.

After identification of the two vertebral bodies which are to be fused together, the surgeon identifies an implant of desired size and determines the appropriate amount of distraction to be applied between the vertebrae before placement of the implant. The appropriate amount of distraction to be applied between vertebral bodies can be determined by incrementally distracting the affected vertebrae using a series of incrementally sized distraction spacers until the desired distraction is reached.

As discussed, above, distraction spacers suitable for the invention are known. The distraction spacers can be inserted and removed from the disk space using, for example, a distraction spacer handle 28, as shown in FIG. 21 of U.S. Pat. No. 5,489,307. Once the desired distraction spacer size is determined, the distraction spacer is attached to a reduced lateral profile obturator 100 shown in FIGS. 4–7. An identically sized distraction spacer is also attached to the distal end of a cylindrical obturator such as 150 of FIGS. 9–10. After attaching a distraction spacer to each obturator, the distal ends of both obturators are oriented in the same direction and the cylindrical obturator 150 is held against the flat surface 121 of the RLP obturator 100 such that the longitudinal axis of each obturator (X—X and Y—Y) are parallel. Holding the two obturators together as a single unit, the distal ends of the attached distraction spacers are aligned flush with one another as diagrammatically illustrated in FIG. 15.

As a unit, the surgeon visually identifies the midpoint between the longitudinal axes (X—X and Y—Y) passing through the distraction spacers. The midpoint is then aligned with the midline of the disk space and the distraction plugs inserted into the intervertebral disk space by tapping on the proximal ends of the obturators.

Figure 16:
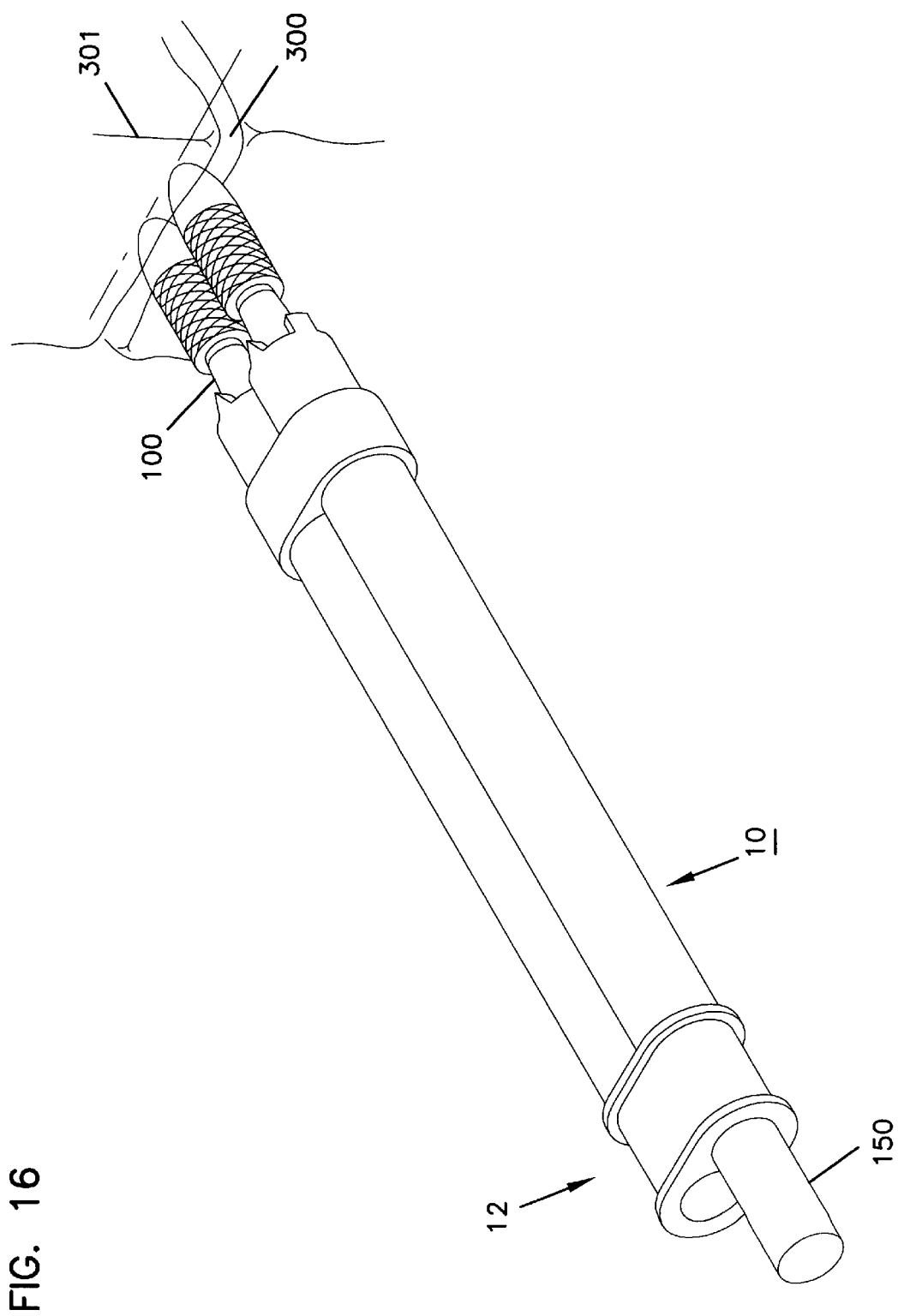
FIG. 16 is a perspective view of a multi-lumen guide and obturator assembly at the anterior margins of opposing vertebral bodies.
Figure 17:
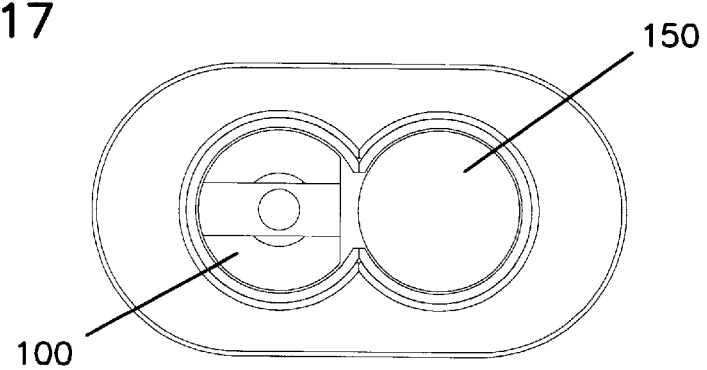
FIG. 17 is a proximal end-on view of a reduced lateral profile obturator and a cylindrical obturator within the multi-lumen guide.

Referring to FIG. 16, once the obturators are secured in the disk space 300 with the proximal edge of the distraction spacers approximately flush with the anterior margin 301 of the vertebral bodies, the multi-lumen guide is passed over the obturators until the attachment arrangement at the distal end of the multi-lumen guide is near the anterior margins of the vertebral bodies on either side of the affected disk space. After verifying that all soft tissue structures are free of damage by the anchoring arrangement, the multi-lumen guide is tapped into the vertebrae. If paddles (26 and 30 of FIGS. 1 and 2) are present, they are oriented to pass into the disk space. Once the multi-lumen guide 10 is secured, the cylindrical obturator 150 is removed. The surgeon's view through the multi-lumen guide before removing obturator 150 is illustrated in FIG. 17.

It will be appreciated from FIG. 16 that, preferably, the length of shaft 105 of the RLP obturator 100 is such that when within multi-lumen guide 10, the proximal end 111 of shaft 105 is flush with or extends minimally beyond the proximal end of the multi-lumen guide to permit the surgeon freedom to work in the right surgical field lumen without interference from the proximal end of the RLP obturator 100 that is still in place. Distraction of the disk space on the right after the obturator 150 has been removed is maintained by the combination of the distraction spacer attached to the remaining obturator 100 and the anchoring arrangement of the multi-lumen guide that is embedded in the vertebral bodies.

After verifying that the flat surface of the RLP obturator 100 is oriented medially and parallel to the sagittal plane of the vertebral column, a drill depth guide, such as a spacer cap illustrated in FIGS. 11–14, can be placed on the proximal end 12 of the multi-lumen guide. As discussed previously, the surgeon selects the appropriate spacer cap size for providing the desired depth of drilling into the vertebral bodies.

A reamer, drill or other boring tool can then be passed through the multi-lumen guide to form a bore between opposing vertebral bodies. Suitable reamers including starter vertebral reamers, final vertebral reamers, guide pins and methods of using these instruments, are disclosed in, for example, U.S. Pat. No. 5,489,307. Threads can also be tapped into the bore using a bone tap such as those described in U.S. Pat. No. 5,489,307.

Figure 18:
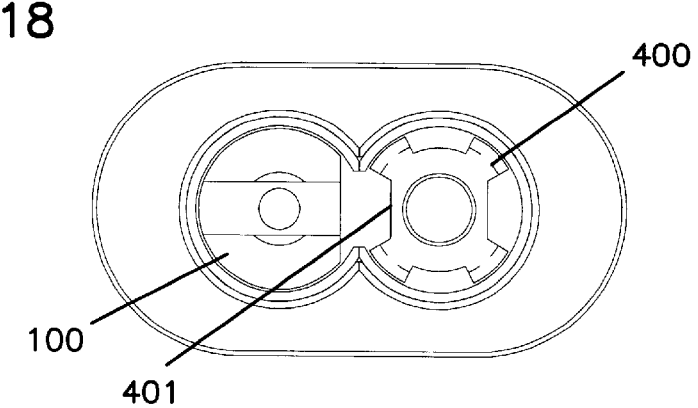
FIG. 18 is a proximal end-on view through a multi-lumen guide having a reduced lateral profile obturator on the left side and a reduced lateral profile implant on the right side.
Figure 19:
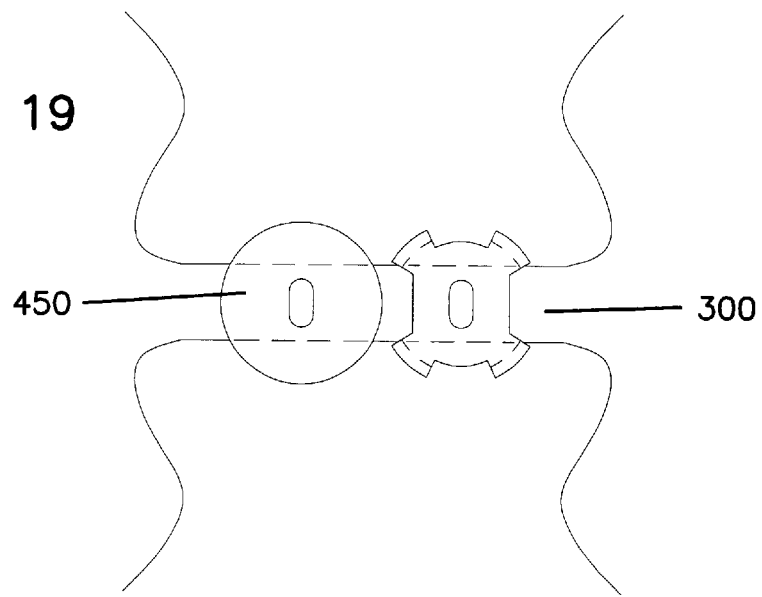
FIG. 19 is an anterior view of an intervertebral disk space between opposing vertebrae that has been implanted with a cylindrical implant on the left side and a reduced lateral profile implant on the right side.

Reduced lateral profile implants suitable for insertion into a bore according to the procedures described herein are disclosed in, for example, U.S. Pat. Nos. 5,609,636; 5,658,337; 5,593,409; and D377,096. If using an implant such as disclosed in U.S. Pat. Nos. 5,604,636 or 5,658,337, the implant can be placed on an implant driver and passed through the multi-lumen guide for insertion into the bore. When using an implant such as those disclosed in U.S. Pat. Nos. 5,604,636 and 5,658,337, prior to removing the implant driver from the implant, the surgeon should ensure that the handle of the implant driver is in parallel alignment with the disk space. After removing the implant driver, preferably the inserted RLP implant 400 is oriented such that the reduced profile surface 401 is facing the flat surface 121 of the RLP obturator 100 as diagrammatically illustrated in FIG. 18. Subsequently, the RLP obturator 100 is removed from the multi-lumen guide 10. Removal of the obturator can be facilitated by attachment of a handle such as the T-handle 140 illustrated in FIG. 8. After removing the obturator 100, a drill depth guide can be placed on the proximal end of the multi-lumen guide, a bore drilled, and the steps described above repeated on the second side. A second reduced lateral profile implant can then be inserted into the tap bore. Alternatively, a cylindrical implant can be inserted into the second bore. In the latter case, the reduced lateral profile implant is inserted first and the cylindrical implant second. FIG. 19 diagrammatically illustrates an anterior view of disk space 300 between opposing vertebrae implanted with a cylindrical implant 450 on the left and a reduced lateral profile implant 400 on the right.

While the foregoing discussion is directed to preparing a threaded bore for insertion of a threaded implant, non-threaded implant bores can also be prepared according to the invention for impact fitted implants.

It will be apparent to one of ordinary skill in the art that many changes and modifications can be made in the invention without departing from the spirit or scope of the appended claims.

We claim:

1. A multi-lumen guide for implanting a spinal fusion device between opposing vertebral bodies, the multi-lumen guide comprising:

a first elongate lumen having a first cross sectional geometry;

a second elongate lumen having a second cross sectional geometry;

the second elongate lumen being adjacent and parallel to the first elongate lumen;

the first cross sectional geometry and the second cross sectional geometry overlap;

the first elongate lumen defined by a first wall and the second elongate lumen defined by a second wall, the first wall having a first wall opening between the first elongate lumen and an exterior surface of the multi-lumen guide.

2. The multi-lumen guide according to claim 1 wherein the first cross sectional geometry of the first elongate lumen is circular.

3. The multi-lumen guide according to claim 1 having a first end with an anchoring arrangement for securing the multi-lumen guide to the vertebral bodies.

4. The multi-lumen guide according to claim 3 wherein the anchoring arrangement comprises at least two teeth.

5. The multi-lumen guide according to claim 3 wherein the first end further comprises at least one lateral paddle.

6. The multi-lumen guide according to claim 5 wherein the first end comprises two diametrically opposing lateral paddles.

7. The multi-lumen guide according to claim 1 wherein the first wall opening is an elongate slot.

8. The multi-lumen guide according to claim 7 wherein the second wall has a second wall opening between the second elongate lumen and the exterior surface of the multi-lumen guide and wherein the first wall opening and the second wall opening face one another.

9. A kit for placement of a spinal implant between opposing vertebral bodies, the kit comprising:

a multi-lumen guide comprising:
(i) a first elongate lumen having a first cross sectional geometry;
(ii) a second elongate lumen having a second cross sectional geometry;
(iii) the second elongate lumen being adjacent and parallel to the first elongate lumen; and
(iv) the first cross sectional geometry and the second cross sectional geometry overlap;

a first obturator having a cross-sectional configuration allowing passage of the first obturator into the first elongate lumen, the cross-sectional configuration of the first obturator being substantially cylindrical;

a second obturator having a cross-sectional configuration allowing passage of the second obturator into the first elongate lumen and having a flat side parallel to a longitudinal axis of the second obturator.

10. A kit according to claim 9 wherein the first obturator has a first end including a handle and a second end including a threaded protuberance.

11. A kit according to claim 10 further comprising a distraction spacer.

12. A kit according to claim 11 wherein the distraction spacer includes a threaded bore for receiving the threaded protuberance of the first obturator.

13. A kit according to claim 9 wherein the first obturator and second obturator are different lengths.

14. A kit according to claim 9 further comprising a spacer cap.

15. A kit according to claim 14 wherein the spacer cap comprises a hollow oval body having
(i) a first end and a second end;
(ii) an interior surface and an exterior surface, the interior surface having an axially projecting shoulder;
(iii) a first longitudinal wall diametrically opposite a second longitudinal wall; and
(iv) a first curved wall diametrically opposite a second curved wall.

16. A kit according to claim 15 wherein the first curved wall has a slot therethrough.

17. A method for implanting a spinal implant into a disk space between opposing vertebral bodies the method comprising:

placing a first distraction spacer into a first side of a disk space between opposing vertebral bodies;

placing a second distraction spacer into a second side of a disk space between opposing vertebral bodies;

mounting a distal end of a first obturator to a selected one of the first and second distraction spacers, the first obturator having a cross-sectional configuration which is substantially cylindrical;

positioning a multi-lumen guide over the first obturator, the multi-lumen guide comprising:
(i) a first elongate lumen having a first cross sectional geometry;
(ii) a second elongate lumen having a second cross sectional geometry;
(iii) the second elongate lumen being adjacent and parallel to the first elongate lumen; and
(iv) the first cross sectional geometry and the second cross sectional geometry overlap;

and removing a selected one of the first distraction spacer and the second distraction spacer from the disk space for boring a hole between opposing vertebral bodies on the side of the removed distraction spacer.

18. A method according to claim 17 wherein the first and second distraction spacers are placed in the disk space between opposing vertebral bodies simultaneously.

19. A method according to claim 17 wherein the first guide lumen and the second guide lumen are fixed together with a collar.

20. A method according to claim 17 wherein the first guide lumen and the second guide lumen are fixed together prior to positioning the multi-lumen guide over the first obturator.

21. A method according to claim 17 wherein the first obturator is mounted to the selected one of the first and second distraction spacers before the multi-lumen guide is positioned over the first obturator.

22. A method according to claim 17 further comprising a step of mounting a distal end of a second obturator to a selected one of the first and second distraction spacers, the second obturator having a flat side parallel to a longitudinal axis of the second obturator.

23. A method according to claim 22 wherein the second obturator is mounted to the distraction spacer before the multi-lumen guide tube is positioned over the first obturator.

* * * * *